US010575731B2

(12) United States Patent
Emken et al.

(10) Patent No.: US 10,575,731 B2
(45) Date of Patent: Mar. 3, 2020

(54) USE OF A SENSOR WITH MULTIPLE EXTERNAL SENSOR TRANSCEIVER DEVICES

(71) Applicant: Senseonics, Incorporated, Germantown, MD (US)

(72) Inventors: Jeremy Emken, Germantown, MD (US); Philip Huffstetler, Germantown, MD (US); Todd Whitehurst, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 0 days.

(21) Appl. No.: 15/905,343

(22) Filed: Feb. 26, 2018

(65) Prior Publication Data

US 2018/0177396 A1 Jun. 28, 2018

Related U.S. Application Data

(62) Division of application No. 14/510,587, filed on Oct. 9, 2014, now Pat. No. 9,901,250.

(60) Provisional application No. 61/888,668, filed on Oct. 9, 2013.

(51) Int. Cl.
*A61B 5/1455* (2006.01)
*H04W 84/18* (2009.01)
*A61B 5/00* (2006.01)
*A61B 5/145* (2006.01)
*H04W 8/00* (2009.01)
*H04L 29/08* (2006.01)

(52) U.S. Cl.
CPC .......... *A61B 5/0002* (2013.01); *A61B 5/0031* (2013.01); *A61B 5/1455* (2013.01); *A61B 5/14532* (2013.01); *A61B 5/6846* (2013.01); *H04L 67/125* (2013.01); *H04L 67/18* (2013.01); *H04W 8/005* (2013.01); *A61B 2560/0252* (2013.01); *A61B 2562/08* (2013.01); *A61B 2562/085* (2013.01); *H04W 84/18* (2013.01)

(58) Field of Classification Search
CPC ........ A61B 2560/0252; A61B 2562/08; A61B 2562/085; A61B 5/0002; A61B 5/0031; A61B 5/14532; A61B 5/1455; A61B 5/6846; H04L 67/125; H04L 67/18; H04W 84/18; H04W 8/005
USPC ....................................................... 600/302
See application file for complete search history.

(56) References Cited

U.S. PATENT DOCUMENTS

| 5,512,246 A | 4/1996 | Russell et al. |
| 5,517,313 A | 5/1996 | Colvin, Jr. |
| 5,833,603 A | 11/1998 | Kovacs et al. |

(Continued)

*Primary Examiner* — Navin Natnithithadha
(74) *Attorney, Agent, or Firm* — Rothwell, Figg, Ernst & Manbeck, P.C.

(57) ABSTRACT

Methods, sensors, and systems that prevent or reduce data loss when more than one external sensor transceiver is used with a sensor. A sensor may receive a transceiver identification (ID) of an external transceiver conveyed from the external transceiver and determine whether the received transceiver ID is a new transceiver ID. If sensor determines the received transceiver ID to be a new transceiver ID, the sensor may store the received transceiver ID in a nonvolatile storage medium of the sensor and convey, using the sensor, measurement information stored in the nonvolatile storage medium to the external transceiver.

13 Claims, 8 Drawing Sheets

(56) References Cited

U.S. PATENT DOCUMENTS

| | | | |
|---|---|---|---|
| 6,287,252 B1 * | 9/2001 | Lugo | A61B 5/1112 128/903 |
| 6,308,089 B1 | 10/2001 | von der Ruhr et al. | |
| 6,553,336 B1 | 4/2003 | Johnson et al. | |
| 6,689,056 B1 | 2/2004 | Kilcoyne et al. | |
| 6,764,446 B2 | 7/2004 | Wolinsky et al. | |
| 7,110,823 B2 | 9/2006 | Whitehurst et al. | |
| 7,273,457 B2 | 9/2007 | Penner | |
| 7,640,048 B2 | 12/2009 | Dobbies et al. | |
| 7,641,619 B2 | 1/2010 | Penner | |
| 7,651,596 B2 | 1/2010 | Petisce et al. | |
| 7,656,286 B2 | 2/2010 | Benson et al. | |
| 7,774,145 B2 | 8/2010 | Brauker et al. | |
| 7,811,231 B2 | 10/2010 | Jin et al. | |
| 7,924,150 B2 * | 4/2011 | Baldus | A61B 5/0205 340/539.12 |
| RE42,378 E | 5/2011 | Wolinsky et al. | |
| 8,187,183 B2 | 5/2012 | Jin et al. | |
| 8,291,220 B2 * | 10/2012 | Singh | H04L 9/3273 713/168 |
| 8,323,192 B2 | 12/2012 | Kilcoyne et al. | |
| 8,345,879 B2 * | 1/2013 | Singh | H04L 9/0822 380/279 |
| 8,347,094 B2 * | 1/2013 | Singh | H04L 9/0844 713/169 |
| 8,368,556 B2 | 2/2013 | Sicurello et al. | |
| 8,516,252 B2 * | 8/2013 | Shon | H04L 9/0833 713/168 |
| 8,622,903 B2 | 1/2014 | Jin et al. | |
| 8,771,183 B2 | 7/2014 | Sloan | |
| 8,830,053 B2 * | 9/2014 | Benson | G05B 13/0275 340/506 |
| 8,994,556 B2 | 3/2015 | Lundy | |
| 9,088,452 B2 | 7/2015 | Sicurello et al. | |
| 9,386,522 B2 | 7/2016 | San Vicente et al. | |
| 9,390,608 B2 | 7/2016 | Lundy | |
| 9,633,197 B2 * | 4/2017 | Lakshmanan | H04W 4/029 |
| 9,693,688 B2 | 7/2017 | Sicurello et al. | |
| 9,730,160 B2 | 8/2017 | San Vicente et al. | |
| 2002/0045921 A1 | 4/2002 | Wolinsky et al. | |
| 2002/0177782 A1 | 11/2002 | Penner | |
| 2003/0229383 A1 | 12/2003 | Whitehurst et al. | |
| 2004/0133089 A1 | 7/2004 | Kilcoyne et al. | |
| 2004/0186365 A1 | 9/2004 | Jin et al. | |
| 2005/0182306 A1 | 8/2005 | Sloan | |
| 2006/0291657 A1 * | 12/2006 | Benson | G05B 13/0275 380/270 |
| 2007/0002139 A1 * | 1/2007 | Benson | G05B 13/0275 348/143 |
| 2007/0008410 A1 * | 1/2007 | Benson | G05B 13/0275 348/143 |
| 2007/0182544 A1 * | 8/2007 | Benson | G05B 13/0275 340/521 |
| 2008/0015421 A1 | 1/2008 | Penner | |
| 2009/0268911 A1 * | 10/2009 | Singh | H04L 9/0844 380/270 |
| 2009/0268914 A1 * | 10/2009 | Singh | H04L 9/0822 380/279 |
| 2009/0271622 A1 * | 10/2009 | Singh | H04L 9/3273 713/168 |
| 2010/0277342 A1 | 11/2010 | Sicurello et al. | |
| 2011/0028817 A1 | 2/2011 | Jin et al. | |
| 2012/0232368 A1 | 9/2012 | Jin et al. | |
| 2013/0076531 A1 | 3/2013 | San Vicente et al. | |
| 2013/0076532 A1 | 3/2013 | San Vicente et al. | |
| 2013/0078912 A1 | 3/2013 | San Vicente et al. | |
| 2013/0211788 A1 | 8/2013 | Sicurello et al. | |
| 2014/0024908 A1 | 1/2014 | Hagi | |
| 2016/0259932 A1 * | 9/2016 | Lakshmanan | H04W 4/029 |

* cited by examiner

USE OF A SENSOR WITH MULTIPLE EXTERNAL SENSOR TRANSCEIVER DEVICES

CROSS-REFERENCE TO RELATED APPLICATION

The present application is a divisional of U.S. patent application Ser. No. 14/510,587, filed Oct. 9, 2014, which claims the benefit of priority to U.S. Provisional Application Ser. No. 61/888,668, filed on Oct. 9, 2013, which are incorporated herein by reference in their entireties.

BACKGROUND

Field of Invention

The present invention relates generally to use of multiple external sensor transceivers with a sensor. Specifically, the present invention relates to determining whether an external sensor transceiver is a new external sensor transceiver and, if so, conveying stored measurement information to the new external sensor transceiver.

Discussion of the Background

A sensor may be implanted within a living animal (e.g., a human) used to measure the concentration of an analyte (e.g., glucose or oxygen) in a medium (e.g., interstitial fluid (ISF) or blood) within the living animal. The sensor may include a light source (e.g., a light-emitting diode (LED) or other light emitting element), indicator molecules, and a photodetector (e.g., a photodiode, phototransistor, photoresistor or other photosensitive element). Examples of implantable sensors employing indicator molecules to measure the concentration of an analyte are described in U.S. Pat. Nos. 5,517,313 and 5,512,246, which are incorporated herein by reference in their entirety.

Data transfer occurs between an implanted sensor and an external sensor transceiver only when the external sensor transceiver is in the proximity of the implanted sensor. Different external sensor transceivers may be used to obtain analyte measurement information from an implanted sensor (e.g., if an external sensor transceiver stops working or a patient changes doctors). When more than one external sensor transceiver is used to obtain analyte information from an implanted sensor, measurement information may be lost (e.g., previous analyte measurement readings). However, the implanted sensor has no way of detecting when the external sensor transceiver has changed.

There is presently a need in the art for a sensor capable of being used with multiple external sensor transceivers while reducing and/or eliminating loss of measurement information and/or calibration parameters.

SUMMARY

One aspect of the invention may provide a method of using a first node in a system having two or more nodes, the method may include receiving, by the first node, a unique identification code from a second node in the system. The method may include determining, by the first node, whether the second node is a new node that has not previously communicated with the first node based on the received unique identification code.

Another aspect of the invention may provide a method of using a sensor in a living animal. The method may include receiving, using the sensor, a transceiver identification (ID) of an external transceiver conveyed from the external transceiver. The method may include determining, using the sensor, whether the received transceiver ID is a new transceiver ID. The method may include, if the received transceiver ID is determined to be a new transceiver ID, storing, using the sensor, the received transceiver ID in a nonvolatile storage medium of the sensor. The method may include, if the received transceiver ID is determined to be a new transceiver ID, conveying, using the sensor, measurement information stored in the nonvolatile storage medium to the external transceiver.

In some embodiments, determining whether the received transceiver ID is a new transceiver ID may comprise determining whether the received transceiver ID matches a transceiver ID previously stored to the nonvolatile storage medium of the sensor. In some embodiments, the sensor may convey the measurement information stored in the nonvolatile storage medium to the external transceiver only if the received transceiver ID is determined to be a new transceiver ID.

Still another aspect of the invention may provide a sensor including an inductive element and circuitry. The circuitry may include a non-volatile storage medium. The circuitry may be configured to: receive a transceiver identification (ID) of an external transceiver conveyed from the external transceiver; determine whether the received transceiver ID is a new transceiver ID; if the received transceiver ID is determined to be a new transceiver ID, store the received transceiver ID in the nonvolatile storage medium; and, if the received transceiver ID is determined to be a new transceiver ID, convey, using the inductive element, measurement information stored in the nonvolatile storage medium to the external transceiver.

In some embodiments, the circuitry may be configured to determine whether the received transceiver ID is a new transceiver ID by determining whether the received transceiver ID matches a transceiver ID previously stored to the nonvolatile storage medium. In some embodiments, the circuitry may be configured to convey the measurement information stored in the nonvolatile storage medium to the external transceiver only if circuitry determines the received transceiver ID is a new transceiver ID.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
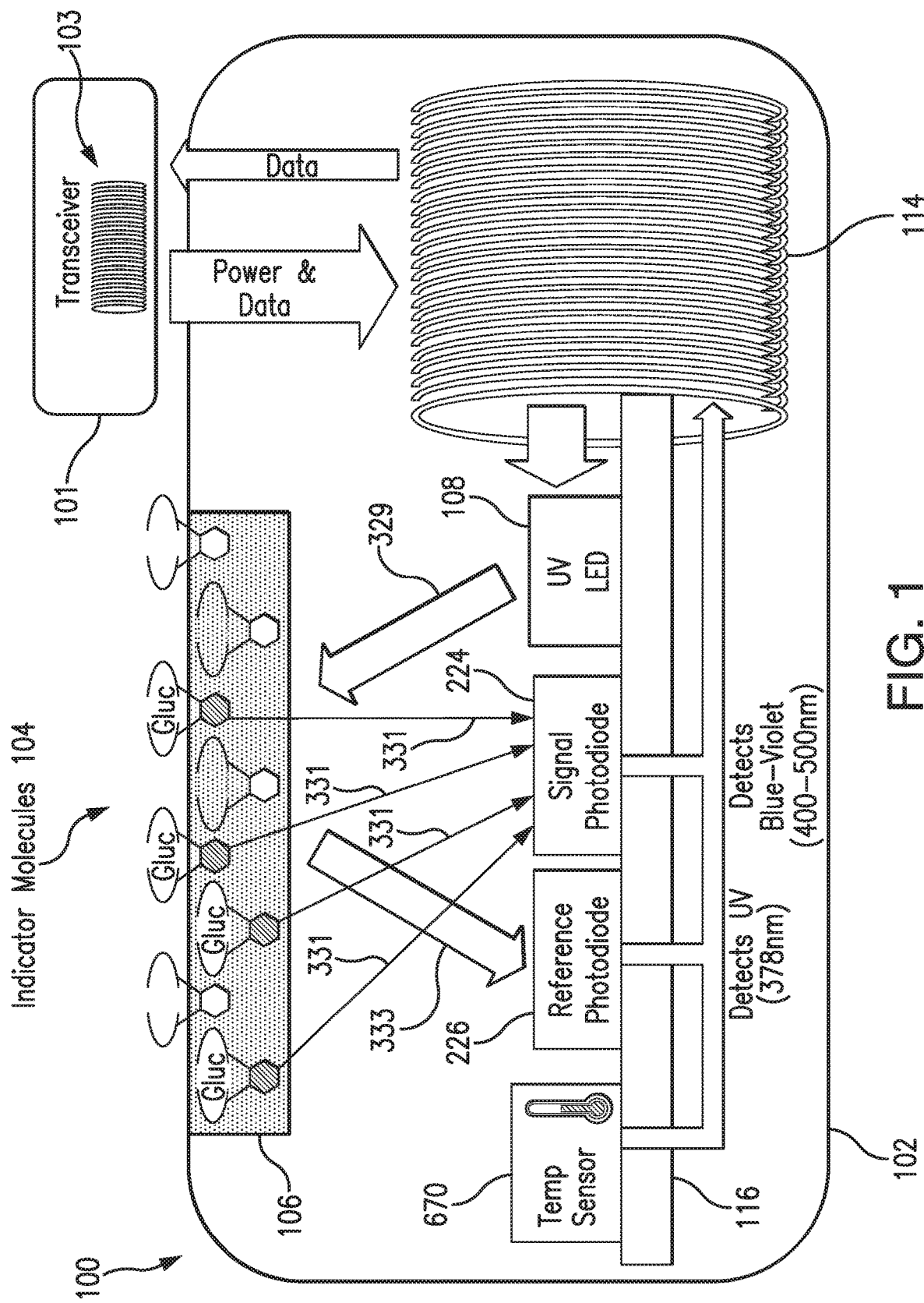
FIG. 1 is a schematic view illustrating a sensor system embodying aspects of the present invention.
Figure 2:
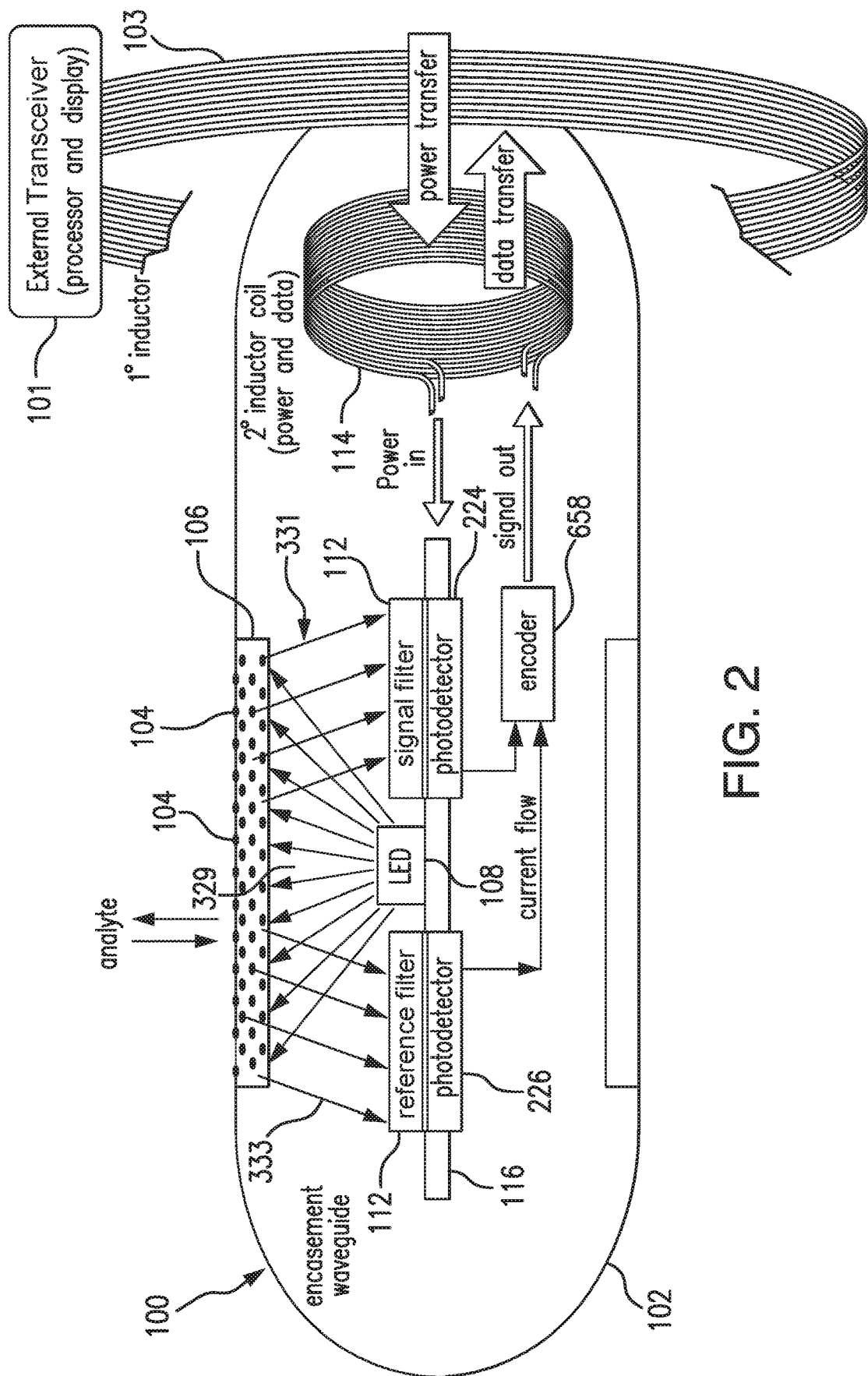
FIG. 2 is a schematic view illustrating a sensor system embodying aspects of the present invention.

FIGS. 1 and 2 are schematic views of sensor systems embodying aspects of the present invention. In one non-limiting embodiment, the system includes a sensor 100 and an external sensor transceiver 101. In the embodiments shown in FIGS. 1 and 2, the sensor 100 may be in a living animal (e.g., implanted in a living human). The sensor 100 may be, for example, in a living animal's arm, wrist, leg, abdomen, or other region of the living animal suitable for sensor implantation or insertion. For example, in one non-limiting embodiment, the sensor 100 may be implanted subcutaneously. In some embodiments, the sensor 100 may be an optical sensor (e.g., a fluorometer). The sensor 100 may be configured to determine a concentration of an analyte (e.g., glucose or oxygen) in a medium (e.g., interstitial fluid or blood) of the living animal. In some embodiments, the sensor 100 may be a chemical or biochemical sensor.

A sensor transceiver 101 may be an electronic device that communicates with the sensor 100 to power the sensor 100 and/or obtain analyte (e.g., glucose) readings from the sensor 100. In non-limiting embodiments, the transceiver 101 may be a handheld transceiver, a wristwatch, an armband, or other device placed in close proximity to the sensor 100. In one embodiment, positioning (i.e., hovering or swiping/waiving/passing) the transceiver 101 within range over the sensor implant site (i.e., within proximity of the sensor 100) will cause the transceiver 101 to automatically convey a measurement command to the sensor 100 and receive a reading from the sensor 100.

In some embodiments, the sensor transceiver 101 may include an inductive element 103, such as, for example, a coil. The sensor transceiver 101 may generate an electromagnetic wave or electrodynamic field (e.g., by using a coil) to induce a current in an inductive element 114 of the sensor 100, which powers the sensor 100 (e.g., through an inductive link of, for example, 13.56 MHz). The sensor transceiver 101 may also convey data (e.g., commands) to the sensor 100. For example, in a non-limiting embodiment, the sensor transceiver 101 may convey data by modulating the electromagnetic wave used to power the sensor 100 (e.g., by modulating the current flowing through a coil 103 of the sensor transceiver 101). The modulation in the electromagnetic wave generated by the transceiver 101 may be detected/extracted by the sensor 100. Moreover, the sensor transceiver 101 may receive data (e.g., measurement information) from the sensor 100. For example, in a non-limiting embodiment, the sensor transceiver 101 may receive data by detecting modulations in the electromagnetic wave generated by the sensor 100, e.g., by detecting modulations in the current flowing through the coil 103 of the sensor transceiver 101.

The inductive element 103 of the sensor transceiver 101 and the inductive element 114 of the sensor 100 may be in any configuration that permits adequate field strength to be achieved when the two inductive elements are brought within adequate physical proximity. For example, in one non-limiting embodiment, as illustrated in FIG. 2, the inductive element 103, which may be in a wrist band or arm band, may wrap around the sensor 100. However, this is not required, and, in alternative embodiments, as illustrated in FIG. 1, the inductive element 103 does not wrap around the sensor 100.

The external sensor transceiver 101 may read measured analyte (e.g., glucose) data from a subcutaneous sensor 100. After reading the values are read from the sensor 100, the external sensor transceiver may process, store, and/or display the data. In some embodiments, the external sensor transceiver 101 may also transmit data (e.g., via USB port) to a personal computer (PC) for further processing and/or display. Clinical technicians and/or doctors may use the external transceiver 101 to monitor their patients' glucose readings by uploading history logs from a transceiver 101 to a PC application for review and analysis. In some embodiments, doctors may have the option to set up alert profiles for their patients. Patients may read the analyte value displayed on the external sensor transceiver 101 and may view alerts and warnings are set up by the doctor or themselves.

In some embodiments, a unique transceiver identification (ID) may be associated with the external sensor transceiver 101, and the external sensor transceiver 101 may be configured to convey the transceiver ID (e.g., using the inductive element 103) to the sensor 100. In some embodiments, the sensor 100 may use the unique transceiver ID to distinguish the external sensor transceiver 101 from other external sensor transceivers that may also be used to convey power and data to the sensor 100 and receive data from the sensor 100. In some non-limiting embodiments, the sensor 100 may use the unique transceiver ID to determine whether the external sensor transceiver 101 is a new sensor transceiver (e.g., an external sensor transceiver 101 that has not previously been used with the sensor 100 or is different than the external sensor transceiver 101 last used with the sensor 100).

In one non-limiting embodiment, sensor 100 includes a sensor housing 102 (i.e., body, shell, capsule, or encasement), which may be rigid and biocompatible. In exemplary embodiments, sensor housing 102 may be formed from a suitable, optically transmissive polymer material, such as, for example, acrylic polymers (e.g., polymethylmethacrylate (PMMA)). In some embodiments, the sensor housing 102 may any shape suitable for implantation or insertion into a living animal. For instance, in some non-limiting embodiments, the sensor housing 102 may be cylindrical, pill-shaped, disc-shaped, spherical, or rectangular prism-shaped.

In some embodiments, the sensor 100 includes indicator molecules 104. Indicator molecules 104 may be fluorescent indicator molecules (e.g., Trimethyltrifluromethylsilane (TFM) fluorescent indicator molecules) or absorption indicator molecules. In some embodiments, the indicator molecules 104 may reversibly bind an analyte (e.g., glucose). When an indicator molecule 104 has bound the analyte, the indicator molecule may become fluorescent, in which case the indicator molecule 104 is capable of absorbing (or being excited by) excitation light 329 and emitting light 331. In one non-limiting embodiment, the excitation light 329 may have a wavelength of approximately 378 nm, and the emission light 331 may have a wavelength in the range of 400 to 500 nm. When no glucose is bound, the indicator molecule 104 may be only weakly fluorescent.

In some non-limiting embodiments, sensor 100 may include a polymer graft/matrix layer 106 coated, diffused, adhered, or embedded on at least a portion of the exterior surface of the sensor housing 102, with the indicator molecules 104 distributed throughout the polymer graft 106. In some embodiments, the polymer graft 106 may be a fluorescent analyte indicating polymer. In one non-limiting embodiment, the polymer may be biocompatible and stable, grafted onto the surface of sensor housing 102, designed to allow for the direct measurement of interstitial fluid (ISF) glucose after subcutaneous implantation of the sensor 100.

In some embodiments, the sensor 100 may include a light source 108, which may be, for example, a light emitting diode (LED) or other light source, that emits radiation, including radiation over a range of wavelengths that interact with the indicator molecules 104. In other words, the light source 108 may emit the excitation light 329 that is absorbed by the indicator molecules 104 in the polymer graft 106. As noted above, in one non-limiting embodiment, the light source 108 may emit excitation light 329 that is ultraviolet (UV) light (e.g., light with a wavelength of approximately 378 nm). In one embodiment, the graft 106 may be positioned to receive excitation light 329 emitted by the light source 108.

In some embodiments, the sensor 100 may also include one or more photodetectors (e.g., photodiodes, phototransistors, photoresistors or other photosensitive elements). For example, in the embodiment illustrated in FIGS. 1 and 2, sensor 100 may have a first photodetector 224 and a second photodetector 226. In one non-limiting embodiment, as illustrated in FIGS. 1 and 2, the first photodetector 224 may be a signal photodetector (i.e., read photodetector), and the second photodetector 226 may be a reference photodetector 226. However, the sensor 100 is not required to have more than one photodetector, and, in some alternative embodiments, the sensor 100 may only include the first photodetector 224.

Some part of the excitation light 329 emitted by the light source 108 may be reflected from the polymer graft 106 back into the sensor 100 as reflection light 333, and some part of the absorbed excitation light may be emitted as emitted (fluoresced) light 331. In one non-limiting embodiment, the emitted light 331 may have a higher wavelength than the wavelength of the excitation light 329. The reflected light 333 and emitted (fluoresced) light 331 may be absorbed by the one or more photodetectors (e.g., first and second photodetectors 224 and 226) within the body of the sensor 100.

In some embodiments, the sensor 100 may include one or more filters 112. As illustrated in FIG. 2, each of the one or more photodetectors may be covered by a filter 112. Each of the one or more filters 112 may allow only a certain subset of wavelengths of light to pass through. In some embodiments, the one or more filters 112 may be thin glass filters. In some embodiments, the one or more filters 112 may be thin film (dichroic) filters deposited on the glass and may pass only a narrow band of wavelengths and otherwise reflect most of the light.

In some non-limiting embodiments, the first photodetector 224 may be covered by a filter 112 that is a signal filter. The signal filter may be configured to pass a narrow band of wavelengths including the wavelength of the emission light 331 emitted (e.g., fluoresced) by the indicator molecules 104 in the graft 106. For instance, in one non-limiting embodiment, the peak emission of the indicator molecules 104 may occur around 435 nm, and the signal filter may pass light in the range of 400-500 nm and prevent other light from reaching the first photodetector 224 (e.g., by reflecting most of the light outside the 400-500 nm range). However, this is not required, and, in other embodiments, the emission light 331 may have a different peak emission wavelength, and/or the signal filter may pass light in a different (e.g., narrower, expanded, or shifted) wavelength range.

In some non-limiting embodiments, the second photodetector 226 may be covered by a filter 112 that is a reference filter. The reference filter may be configured to pass a narrow band of wavelengths including the wavelength of a reference light 333. In one non-limiting embodiment, the reference light 333 passed by the reference filter may have the same wavelength as the excitation light 329 (e.g., 378 nm), and the reference filter may pass light in a narrow band (e.g., 350-400 nm) including the wavelength of the excitation light 329 and prevent other light from reaching the second photodetector 226. However, this is not required, and, in other embodiments, the reference light 333 passed by the reference filter may have a different wavelength than the excitation light 329 (e.g., the wavelength of light emitted by reference indicator molecules that are unaffected or generally unaffected by the presence and/or concentration of the analyte), and/or the reference filter may pass light in a different (e.g., narrower, expanded, or shifted) wavelength range.

The first photodetector 224 may be configured to (a) receive the emission light 331 that is emitted from the indicator molecules 104 in the graft 106 and (b) generate a signal indicative of the amount of light received thereby. In some embodiments, higher analyte (e.g., glucose or oxygen) levels/concentrations correspond to a greater amount of emission light 331 (e.g., fluorescence) of the indicator molecules 104 in the graft 106, and, therefore, a greater number of photons striking the first photodetector 224.

The second photodetector 226 may be configured to receive the reference light 333 and generate a signal indicative of the amount of light received thereby. In some embodiments, the reference light 333 may have the same wavelength as the excitation light 329 emitted by the light source 108 and, as illustrated in FIG. 1, may include a portion of the excitation light 329 that is reflected from the graft 106. In some alternative embodiments, the reference light 333 may have a different wavelength than the excitation light 329 (e.g., the wavelength of light emitted by reference indicator molecules that are unaffected or generally unaffected by the presence and/or concentration of the analyte).

In some embodiments, the substrate 116 may be a circuit board (e.g., a printed circuit board (PCB)) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. In some embodiments, the circuitry may include one or more processors (e.g., microprocessors). Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components, may be fabricated in the semiconductor substrate 116 with the remainder of the circuitry is secured to the semiconductor substrate 116, which may provide communication paths between the various secured components. In some embodiments, circuitry of the sensor 100 may incorporate some or all of the structure described in U.S. patent application Ser. No. 13/650,016, which is incorporated herein by reference in its entirety, with particular reference to FIG. 11D.

Figure 3:
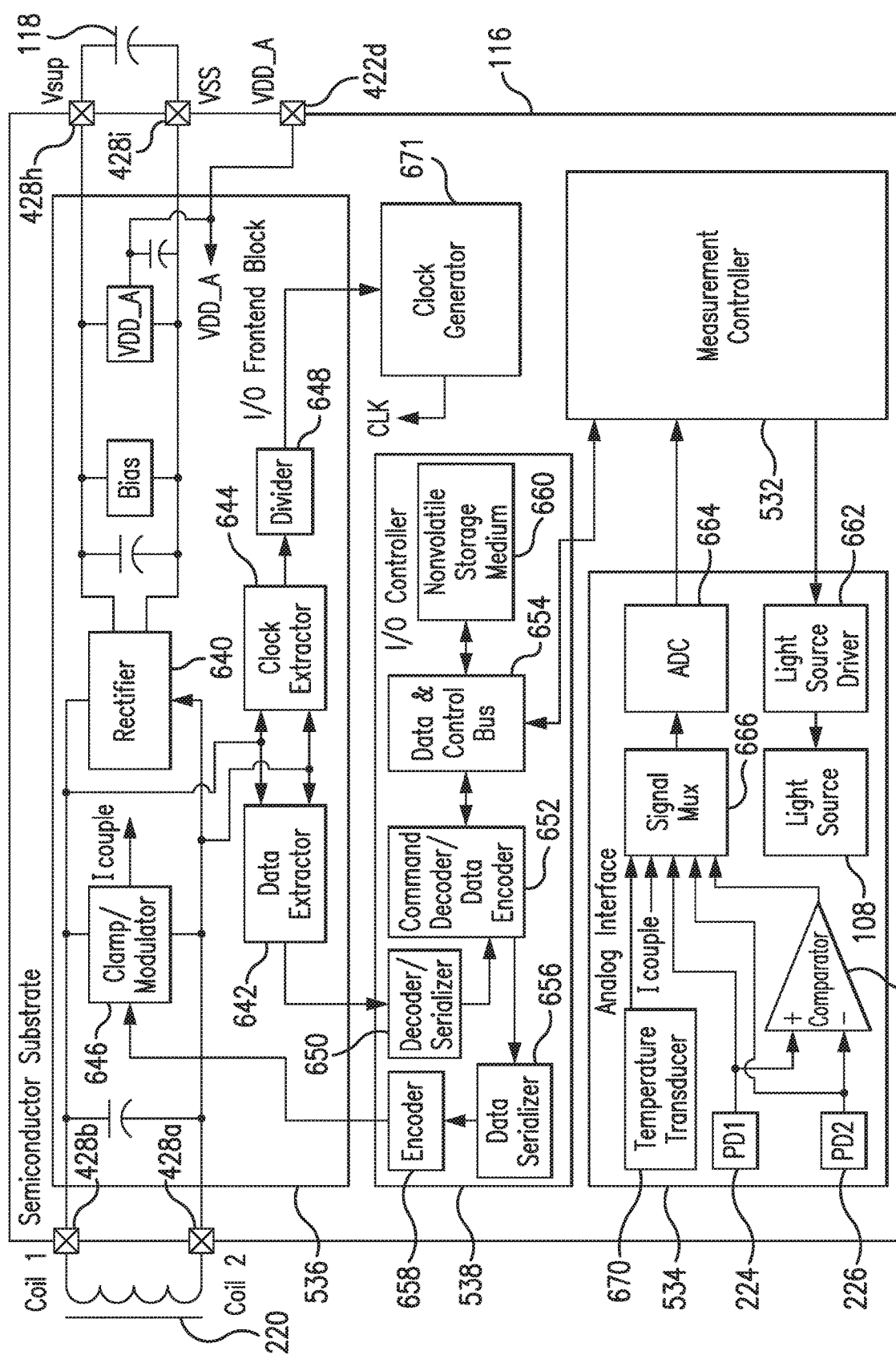
FIG. 3 illustrates a circuit diagram that may be used in accordance with one embodiment of the present invention.

FIG. 3 is block diagram illustrating the functional blocks of the circuitry of sensor 100 according to a non-limiting embodiment in which the circuitry is fabricated in the semiconductor substrate 116. As shown in the embodiment of FIG. 3, in some embodiments, an input/output (I/O) frontend block 536 may be connected to the external inductive element 114, which may be in the form of a coil 220, through coil contacts 428a and 428b. The I/O frontend block 536 may include a rectifier 640, a data extractor 642, a clock extractor 644, clamp/modulator 646 and/or frequency divider 648. Data extractor 642, clock extractor 644 and clamp/modulator 646 may each be connected to external coil 220 through coil contacts 428a and 428b. The rectifier 640 may convert an alternating current produced by coil 220 to a direct current that may be used to power the sensor 100. For instance, the direct current may be used to produce one or more voltages, such as, for example, voltage VDD_A, which may be used to power the one or more photodetectors (e.g., photodetectors 224 and 226). In one non-limiting embodiment, the rectifier 640 may be a Schottky diode; however, other types of rectifiers may be used in other embodiments. The data extractor 642 may extract data from the alternating current produced by coil 220. The clock extractor 644 may extract a signal having a frequency (e.g., 13.56 MHz) from the alternating current produced by coil 220. The frequency divider 648 may divide the frequency of the signal output by the clock extractor 644. For example, in a non-limiting embodiment, the frequency divider 648 may be a 4:1 frequency divider that receives a signal having a frequency (e.g., 13.56 MHz) as an input and outputs a signal having a frequency (e.g., 3.39 MHz) equal to one fourth the frequency of the input signal. The outputs of rectifier 640 may be connected to one or more external capacitors 118 (e.g., one or more regulation capacitors) through contacts 428h and 428i.

In some embodiments, an I/O controller 538 may include a decoder/serializer 650, command decoder/data encoder 652, data and control bus 654, data serializer 656 and/or encoder 658. The decoder/serializer 650 may decode and serialize the data extracted by the data extractor 642 from the alternating current produced by coil 220. The command decoder/data encoder 652 may receive the data decoded and serialized by the decoder/serializer 650 and may decode commands therefrom. The data and control bus 654 may receive commands decoded by the command decoder/data encoder 652 and transfer the decoded commands to the measurement controller 532. The data and control bus 654 may also receive data, such as measurement information, from the measurement controller 532 and may transfer the received data to the command decoder/data encoder 652. The command decoder/data encoder 652 may encode the data received from the data and control bus 654. The data serializer 656 may receive encoded data from the command decoder/data encoder 652 and may serialize the received encoded data. The encoder 658 may receive serialized data from the data serializer 656 and may encode the serialized data. In a non-limiting embodiment, the encoder 658 may be a Manchester encoder that applies Manchester encoding (i.e., phase encoding) to the serialized data. However, in other embodiments, other types of encoders may alternatively be used for the encoder 658, such as, for example, an encoder that applies 8B/10B encoding to the serialized data.

The clamp/modulator 646 of the I/O frontend block 536 may receive the data encoded by the encoder 658 and may modulate the current flowing through the inductive element 114 (e.g., coil 220) as a function of the encoded data. In this way, the encoded data may be conveyed wirelessly by the inductive element 114 as a modulated electromagnetic wave. The conveyed data may be detected by an external reading device by, for example, measuring the current induced by the modulated electromagnetic wave in a coil of the external reading device. Furthermore, by modulating the current flowing through the coil 220 as a function of the encoded data, the encoded data may be conveyed wirelessly by the coil 220 as a modulated electromagnetic wave even while the coil 220 is being used to produce operating power for the sensor 100. See, for example, U.S. Pat. Nos. 6,330,464 and 8,073,548, which are incorporated herein by reference in their entireties and which describe a coil used to provide operative power to an optical sensor and to wirelessly convey data from the optical sensor. In some embodiments, the encoded data is conveyed by the sensor 100 using the clamp/modulator 646 at times when data (e.g., commands) are not being received by the sensor 100 and extracted by the data extractor 642. For example, in one non-limiting embodiment, all commands may be initiated by an external sensor transceiver (e.g., transceiver 101 of FIGS. 1 and 2) and then responded to by the sensor 100 (e.g., after or as part of executing the command). In some embodiments, the communications received by the inductive element 114 and/or the communications conveyed by the inductive element 114 may be radio frequency (RF) communications. Although, in the illustrated embodiments, the sensor 100 includes a single coil 220, alternative embodiments of the sensor 100 may include two or more coils (e.g., one coil for data transmission and one coil for power and data reception).

In an embodiment, the I/O controller 538 may also include a nonvolatile storage medium 660. In a non-limiting embodiment, the nonvolatile storage medium 660 may be an electrically erasable programmable read only memory (EEPROM). However, in other embodiments, other types of nonvolatile storage media, such as flash memory, may be used. The nonvolatile storage medium 660 may receive write data (i.e., data to be written to the nonvolatile storage medium 660) from the data and control bus 654 and may supply read data (i.e., data read from the nonvolatile storage medium 660) to the data and control bus 654. In some embodiments, the nonvolatile storage medium 660 may have an integrated charge pump and/or may be connected to an external charge pump. In some embodiments, the nonvolatile storage medium 660 may store identification information (i.e., traceability or tracking information), measurement information and/or setup parameters (i.e., calibration information). In one embodiment, the identification information may uniquely identify the sensor 100. The unique identification information may, for example, enable full traceability of the sensor 100 through its production and subsequent use. In one embodiment, the nonvolatile storage medium 660 may store calibration information for each of the various sensor measurements. In some embodiments, the nonvolatile storage medium 660 may store one or more transceiver IDs conveyed to the sensor 100. In some non-limiting embodiments, the nonvolatile storage medium 660 may store the date of sensor implant, which may enable a physician to know when the sensor 100 should be replaced.

In some embodiments, the analog interface 534 may include a light source driver 662, analog to digital converter (ADC) 664, a signal multiplexer (MUX) 666 and/or comparator 668. In a non-limiting embodiment, the comparator 668 may be a transimpedance amplifier, in other embodiments, different comparators may be used. The analog interface 534 may also include light source 108, one or more photodetectors (e.g., first and second photodetectors 224 and 226), and/or a temperature sensor 670 (e.g., temperature transducer).

In some embodiments, the one or more photodetectors (e.g., photodetectors 224 and 226) may be mounted on the semiconductor substrate 116, but, in some preferred embodiments, the one or more photodetectors may be fabricated in the semiconductor substrate 116. In some embodiments, the light source 108 may be mounted on the semiconductor substrate 116. For example, in a non-limiting embodiment, the light source 108 may be flip-chip mounted on the semiconductor substrate 116. However, in some embodiments, the light source 108 may be fabricated in the semiconductor substrate 116.

In a non-limiting, exemplary embodiment, the temperature transducer 670 may be a band-gap based temperature transducer. However, in alternative embodiments, different types of temperature transducers may be used, such as, for example, thermistors or resistance temperature detectors. Furthermore, like the light source 108 and one or more photodetectors, in one or more alternative embodiments, the temperature transducer 670 may be mounted on semiconductor substrate 116 instead of being fabricated in semiconductor substrate 116.

The light source driver 662 may receive a signal from the measurement controller 532 indicating the light source current at which the light source 108 is to be driven, and the light source driver 662 may drive the light source 108 accordingly. The light source 108 may emit radiation from an emission point in accordance with a drive signal from the light source driver 662. The radiation may excite indicator molecules 104 distributed throughout the graft 106. The one or more photodetectors (e.g., first and second photodetectors 224 and 226) may each output an analog light measurement signal indicative of the amount of light received by the photodetector. For instance, in the embodiment illustrated in FIG. 3, the first photodetector 224 may output a first analog light measurement signal indicative of the amount of light received by the first photodetector 224, and the second photodetector 226 may output a first analog light measurement signal indicative of the amount of light received by the second photodetector 226. The comparator 668 may receive the first and second analog light measurement signals from the first and second photodetectors 224 and 226, respectively, and output an analog light difference measurement signal indicative of the difference between the first and second analog light measurement signals. The temperature transducer 670 may output an analog temperature measurement signal indicative of the temperature of the sensor 100. The signal MUX 666 may select one of the analog temperature measurement signal, the first analog light measurement signal, the second analog light measurement signal and the analog light difference measurement signal and may output the selected signal to the ADC 664. The ADC 664 may convert the selected analog signal received from the signal MUX 666 to a digital signal and supply the digital signal to the measurement controller 532. In this way, the ADC 664 may convert the analog temperature measurement signal, the first analog light measurement signal, the second analog light measurement signal, and the analog light difference measurement signal to a digital temperature measurement signal, a first digital light measurement signal, a second digital light measurement signal, and a digital light difference measurement signal, respectively, and may supply the digital signals, one at a time, to the measurement controller 532.

In some embodiments, the measurement controller 532 may receive one or more digital measurements and generate measurement information, which may be indicative of the presence and/or concentration of an analyte (e.g., glucose) in a medium in which the sensor 100 is implanted. In some embodiments, the generation of the measurement information may include conversion of a digitized raw signal (e.g., the first digital light measurement signal) into a glucose concentration. For accurate conversion, the measurement controller 532 may take into consideration the optics, electronics, and chemistry of the sensor 100. Further, in some embodiments, the measurement controller 532 may be used to obtain a purified signal of glucose concentration by eliminating noise (e.g., offset and distortions) that is present in the raw signals (e.g., the first digital light measurement signals).

In some embodiments, the circuitry of sensor 100 fabricated in the semiconductor substrate 116 may additionally include a clock generator 671. The clock generator 671 may receive, as an input, the output of the frequency divider 648 and generate a clock signal CLK. The clock signal CLK may be used by one or more components of one or more of the I/O frontend block 536, I/O controller 538, measurement controller 532, and analog interface 534.

In a non-limiting embodiment, data (e.g., decoded commands from the command decoder/data encoder 652 and/or read data from the nonvolatile storage medium 660) may be transferred from the data and control bus 654 of the I/O controller 538 to the measurement controller 532 via transfer registers and/or data (e.g., write data and/or measurement information) may be transferred from the measurement controller 532 to the data and control bus 654 of the I/O controller 538 via the transfer registers.

In some embodiments, the circuitry of sensor 100 may include a field strength measurement circuit. In embodiments, the field strength measurement circuit may be part of the I/O front end block 536, I/O controller 538, or the measurement controller 532 or may be a separate functional component. The field strength measurement circuit may measure the received (i.e., coupled) power (e.g., in mWatts). The field strength measurement circuit of the sensor 100 may produce a coupling value proportional to the strength of coupling between the inductive element 114 (e.g., coil 220) of the sensor 100 and the inductive element of the external transceiver 101. For example, in non-limiting embodiments, the coupling value may be a current or frequency proportional to the strength of coupling. In some embodiments, the field strength measurement circuit may additionally determine whether the strength of coupling/received power is sufficient to perform an analyte concentration measurement and convey the results thereof to the external sensor transceiver 101. For example, in some non-limiting embodiments, the field strength measurement circuit may detect whether the received power is sufficient to produce a certain voltage and/or current. In one non-limiting embodiment, the field strength measurement circuit may detect whether the received power produces a voltage of at least approximately 3V and a current of at least approximately 0.5 mA. However, other embodiments may detect that the received power produces at least a different voltage and/or at least a different current. In one non-limiting embodiment, the field strength measurement circuit may compare the coupling value field strength sufficiency threshold.

In the illustrated embodiment, the clamp/modulator 646 of the I/O circuit 536 acts as the field strength measurement circuit by providing a value (e.g., $I_{couple}$) proportional to the field strength. The field strength value $I_{couple}$ may be provided as an input to the signal MUX 666. When selected, the MUX 666 may output the field strength value $I_{couple}$ to the ADC 664. The ADC 664 may convert the field strength value $I_{couple}$ received from the signal MUX 666 to a digital field strength value signal and supply the digital field strength signal to the measurement controller 532. In this way, the field strength measurement may be made available to the measurement controller 532 and may be used in initiating an analyte measurement command trigger based on dynamic field alignment. However, in an alternative embodiment, the field strength measurement circuit may instead be an analog oscillator in the sensor 100 that sends a frequency corresponding to the voltage level on a rectifier 640 back to the transceiver 101.

In some embodiments, the sensor 100 may be used to obtain accurate analyte measurements (e.g., ISF glucose readings) in patients, and the circuitry of the sensor 100 (which may, for example, include measurement controller 532) may convert the raw signal generated by the photodetector 224 into an analyte (e.g., glucose) concentration. For accurate conversion, the circuitry of the sensor 100 may take into consideration the optics, electronics, and chemistry of the sensor 100. Further, in some embodiments, the circuitry may be used to obtain a purified signal of glucose concentration by eliminating noise (e.g., offset and distortions) that are present in raw signals from the sensor 100.

In some embodiments, the sensor 100 may store measurement information from one or more previous measurements (e.g., in nonvolatile storage medium 660). In some embodiments, the sensor 100 may store one or more transceiver IDs conveyed from one or more external sensor transceivers 101 (e.g., in nonvolatile storage medium 660). In some embodiments, the sensor 100 may use a received transceiver ID to determine whether the external sensor transceiver 101 that conveyed the transceiver ID is a new external sensor transceiver (e.g., an external sensor transceiver 101 that has not previously been used with the sensor 100 or is different than the external sensor transceiver 101 last used with the sensor 100). In some non-limiting embodiments, if the sensor 100 determines that the external sensor transceiver 101 is a new external sensor transceiver, the sensor 100 may store the transceiver ID conveyed from the new external sensor transceiver and/or convey stored measurement information from one or more previous measurements. By doing so, the sensor 100 may eliminate or reduce gaps in measurement information for the new external sensor transceiver.

Figure 4:
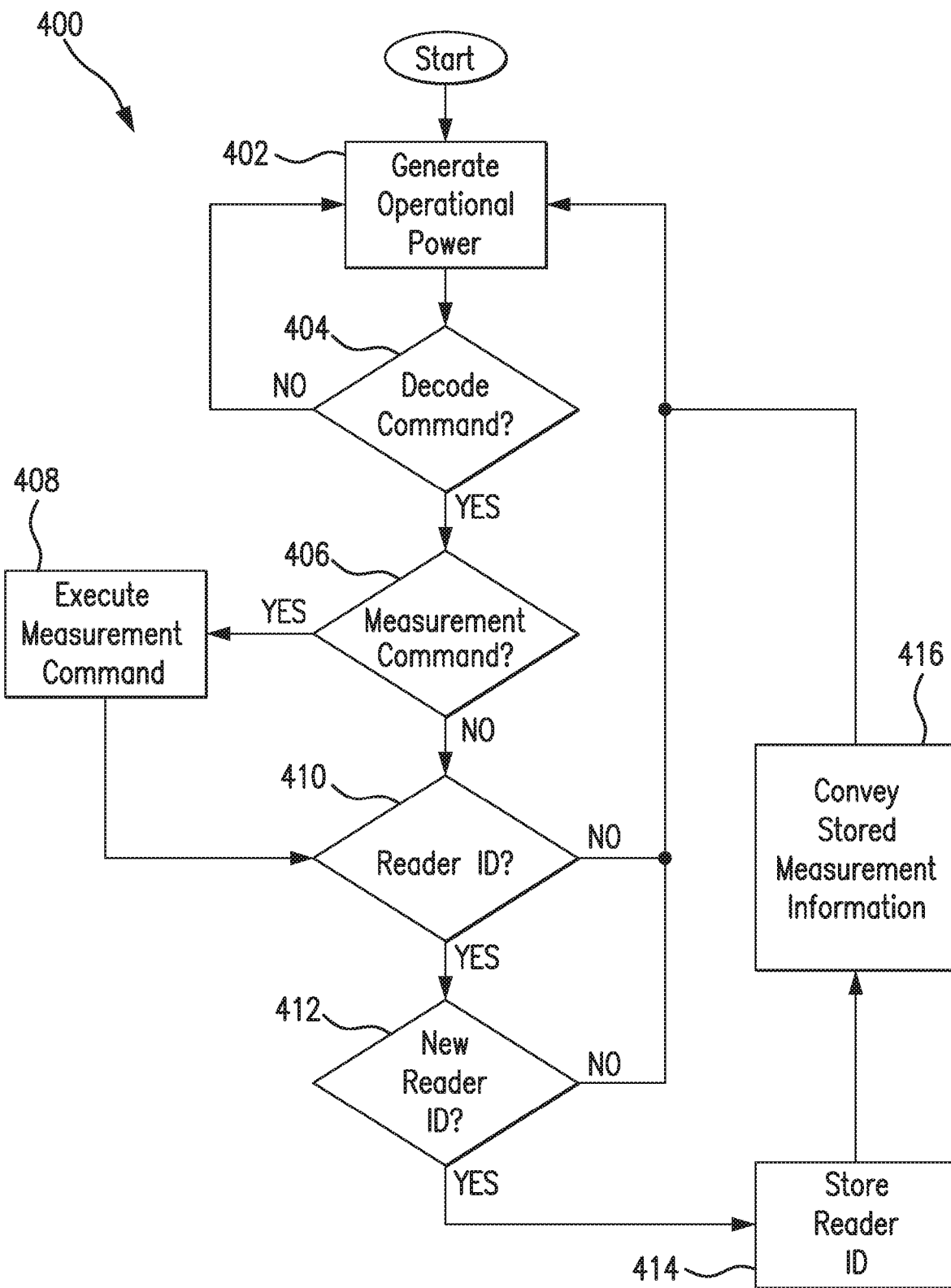
FIG. 4 illustrates a sensor control process that may be performed by the optical sensor in accordance with an embodiment of the present invention.

FIG. 4 illustrates an exemplary sensor control process 400 that may be performed by the sensor 100, which may be, for example, implanted within a living animal (e.g., a living human), in accordance with an embodiment of the present invention. The inductive element 114 of sensor 100 and the inductive element 103 of the external sensor transceiver 101 may be coupled within an electrodynamic field.

The sensor control process 400 may begin with a step 402 of generating operational power using the electrodynamic field. In one embodiment, the electrodynamic field may induce a current in inductive element 114 of sensor 100, and the input/output (I/O) front end block 536 may convert the induced current into power for operating the sensor 100. In a non-limiting embodiment, rectifier 640 may be used to convert the induced current into operating power for the sensor 100.

The sensor control process 400 may include a step 404 in which the sensor 100 determines whether a command has been received (e.g., decoded from modulation of the electrodynamic field). In one non-limiting embodiment, the I/O front end block 536 and I/O controller 538 may convert the induced current into power for operating the sensor 100 and extract and decode any received commands from the induced current. In a non-limiting embodiment, rectifier 640 may be used to convert the induced current into operating power for the sensor 100, data extractor 642 may extract data from the current induced in inductive element 114, decoder/serializer 650 may decode and serialize the extracted data, and command decoder/data encoder 652 may decode one or more commands from the decoded and serialized extracted data. Any decoded commands may then be sent to measurement controller 532 via the data and control bus 654.

Examples of commands that may be received and executed by the sensor 100 may include measurement commands, get result commands, and/or get traceability information commands. The commands may include a transceiver ID identifying the external transceiver 101 that conveyed the command. Examples of measurement commands may include measurement sequence commands (i.e., commands to perform a sequence of measurements and, after finishing the sequence, transmit the resulting measurement information), measure and save commands (i.e., commands to perform a sequence of measurements and, after finishing the sequence, save the resulting measurement information without transmitting the resulting measurement information), and/or single measurement commands (i.e., commands to perform a single measurement). The single measurement commands may be commands to save and/or transmit the measurement information resulting from the single measurement. The measurement commands may or may not include setup parameters (i.e., calibration information). Measurement commands that do not have setup parameters may, for example, be executed using stored setup parameters (e.g., in nonvolatile storage medium 660). Other measurement commands, such as measurement commands to both save and transmit the resulting measurement information, are possible. The commands that may be received and executed by the sensor 100 may also include commands to update the stored the setup parameters. The examples of commands described above are not exhaustive of all commands that may be received and executed by the sensor 100, which may be capable of receiving and executing one or more of the commands listed above and/or one or more other commands.

If a command has not been received, the sensor control process 400 may return to step 402. However, this is not required, and, in an alternative embodiment, if a command has not been received, the sensor control process 400 may proceed to step 410 to determine whether a transceiver ID has been received.

If one or more commands have been received, in step 406, the sensor 100 may determine whether the one or more received commands include a measurement command. If the one or more received commands include a measurement command, in step 408, the sensor 100 may execute the measurement command (e.g., under control of the measurement controller 532). In one non-limiting embodiment, in step 408, the sensor 100 may execute a measurement command execution process 500, which is described in further detail below with reference to FIG. 5.

If the sensor 100 determines in step 406 that the one or more received commands do not include a measurement command (or following completion of measurement command execution in step 408), the sensor 100 may, in a step 410, determine whether a transceiver ID has been received (e.g., decoded from modulation of the electrodynamic field).

The transceiver ID may be conveyed to the sensor 100 as part of a command (e.g., in a transceiver ID field of a command), before or after a command is conveyed is conveyed, or as a separate/independent conveyance.

If the sensor 100 determines in step 410 that a transceiver ID has not been received, the sensor control process 400 may return to step 402. If the sensor 100 determines in step 410 that a transceiver ID has been received, the sensor 100 may, in a step 412, determine whether the received transceiver ID is a new transceiver ID. For example, in non-limiting embodiments, the sensor 100 may determine whether the received transceiver ID is a new transceiver ID by determining whether the received transceiver ID matches a transceiver ID previously stored to the nonvolatile storage medium 660 of the sensor 100. If no transceiver IDs have been previously stored or none of the previously stored transceiver IDs matches the received transceiver ID, the sensor 100 may determine that the received transceiver ID is a new transceiver ID.

For instance, in one non-limiting embodiments, the measurement controller 532 may access any transceiver IDs stored in the nonvolatile storage medium 660 (e.g., via the data and control bus 654) and compare the accessed transceiver ID(s) to the received transceiver ID to determine whether the received transceiver ID has already been stored in the nonvolatile storage medium 660. In one non-limiting alternative embodiment, the sensor 100 may determine that the received transceiver ID is a new transceiver ID if the received transceiver ID is different than the transceiver ID most recently stored to the nonvolatile storage medium 660. In another non-limiting alternative embodiment, the nonvolatile storage medium 660 may store no more than one transceiver ID at a time, and the sensor 100 may determine that the received transceiver ID is a new transceiver ID if the received transceiver ID is different than the one and only transceiver ID stored in the nonvolatile storage medium 660.

If the sensor 100 determines in step 412 that the received transceiver ID is not new, the sensor control process 400 may return to step 402. If the sensor 100 determines in step 412 that the received transceiver ID is new, the sensor 100 may, in a step 414, save the received transceiver ID (e.g., by storing the received transceiver ID in the nonvolatile storage medium 660). For example, in non-limiting embodiments, after comparing the accessed transceiver ID(s) to the received transceiver ID and determining that the received transceiver ID has not already been stored in the nonvolatile storage medium 660 (step 412), the measurement controller 532 may store the received transceiver ID in the nonvolatile storage medium 660 (e.g., via the data and control bus 654). For instance, in one non-limiting embodiment, the measurement controller 532 may output the received transceiver ID to the data and control bus 654, which may transfer the received transceiver ID to the nonvolatile storage medium 660. The nonvolatile storage medium 660 may store the received transceiver ID. In some embodiments, the measurement controller 532 may output, along with the received transceiver ID, an address at which the received transceiver ID is to be saved in the nonvolatile storage medium 660.

In the non-limiting alternative embodiment where the nonvolatile storage medium 660 stores no more than one transceiver ID at a time, saving/storing the received transceiver ID in step 414 may overwrite/replace a previously stored transceiver ID.

If the sensor 100 determines in step 412 that the received transceiver ID is new, the sensor 100 may, in a step 416, convey stored measurement information to the external sensor transceiver 101. For example, in one non-limiting embodiment, after comparing the accessed transceiver ID(s) to the received transceiver ID and determining that the received transceiver ID has not already been stored in the nonvolatile storage medium 660 (step 412), the measurement controller 532 may request stored measurement information. In response to a request from the measurement controller 532, the nonvolatile storage medium 660 may output stored measurement information to the data and control bus 654, and the data and control bus 654 may transfer the retrieved measurement information to the measurement controller 532. The measurement controller 532 may output the retrieved measurement information to the data and control bus 654. The data and control bus 654 may transfer the measurement information to the command decoder/data encoder 652, which may encode the retrieved measurement information. The data serializer 656 may serialize the encoded retrieved measurement information. The encoder 658 may encode the serialized retrieved measurement information. The clamp/modulator 646 may modulate the current flowing through the inductive element 114 (e.g., coil 220) as a function of the encoded retrieved measurement information. In this way, the encoded retrieved measurement information may be conveyed wirelessly by the inductive element 114 as a modulated electromagnetic wave. In some embodiments, the encoded retrieved measurement information wirelessly conveyed by the sensor 100 may be received by the sensor transceiver 1500. In some alternative embodiment, the data and control bus 654 may transfer the retrieved measurement information to the command decoder/data encoder 652 without first transferring the retrieved measurement information to the measurement controller 532.

In some embodiments, the nonvolatile storage medium 660 may contain measurement information from multiple measurements. In some embodiments, in step 416, the sensor 100 may convey the measurement information from the multiple measurements (e.g., new measurement information first or oldest measurement information first). In one embodiment, the sensor 100 may access and convey the measurement information from the multiple measurements one at a time.

In some embodiments, after storing a new transceiver ID (step 414) and conveying stored measurement information (step 416), the sensor control process 400 may return to step 402.

Although not illustrated in FIG. 4, the sensor control process 400 may include additional steps to determine whether the one or more received commands include commands other than a measurement command (e.g., a get result command and/or get traceability information command) and, if so, execute the command(s). Also, although the steps of the sensor control process 400 are illustrated in a particular order in FIG. 4, in alternative embodiments, some steps of the sensor control process 400 may be carried out in a different order. For example, the sensor 100 may convey stored measurement information in step 416 before storing a new transceiver ID in step 414. For another example, the sensor 100 may determine whether a transceiver ID has been received (step 410) before determining whether a measurement command has been received (step 406).

Figure 5:
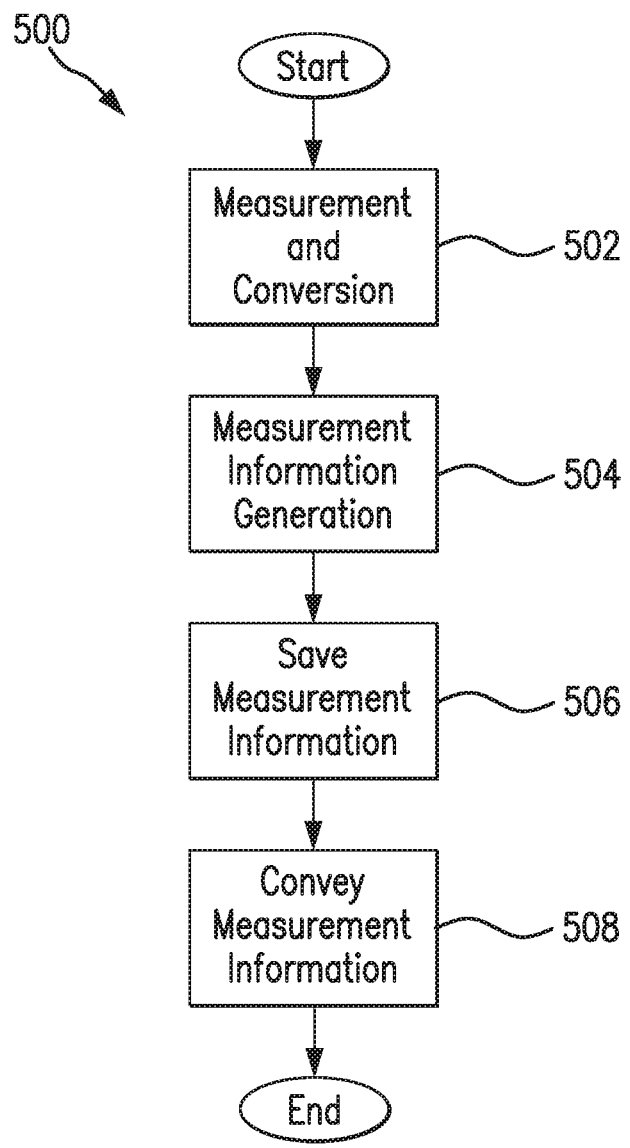
FIG. 5 illustrates a measurement command execution process that may be performed by the sensor to execute a measurement command received by the sensor in accordance with an embodiment of the present invention.

FIG. 5 illustrates a measurement command execution process 500 that may be performed in step 408 of the sensor control process 400 by the sensor 100 to execute a measurement command received by the sensor 100 in accordance with an embodiment of the present invention. In a non-limiting embodiment, the measurement command execution process 500 may begin with a step 502 in which a measurement and conversion process may be performed. The measurement and conversion process may, for example, be performed by the analog interface 534 under control of the measurement controller 532. In one embodiment, the measurement and conversion sequence may include generating one or more analog measurements (e.g., using one or more of temperature transducer 670, light source 108, first photodetector 224, second photodetector 226, and/or comparator 668) and converting the one or more analog measurements to one or more digital measurements (e.g., using ADC 664). One example of the measurement and conversion process that may be performed in step 502 is described in further detail below with reference to FIG. 6.

At step 504, the sensor 100 may generate measurement information in accordance with the one or more digital measurements produced during the measurement and conversion sequence performed in step 502. Depending on the one or more digital measurements produced in step 502, the measurement information may be indicative of the presence and/or concentration of an analyte in a medium in which the sensor 100 is implanted. In one embodiment, in step 504, the measurement controller 532 may receive the one or more digital measurements and generate the measurement information.

In some embodiments, the measurement command execution process 500 may include a step 506 in which the sensor 100 saves the measurement information generated in step 504. In one non-limiting embodiment, in step 506, the measurement controller 532 may output the measurement information to the data and control bus 654, which may transfer the measurement information to the nonvolatile storage medium 660. The nonvolatile storage medium 660 may save the received measurement information. In some embodiments, the measurement controller 532 may output, along with the measurement information, an address at which the measurement information is to be saved in the nonvolatile storage medium 660. In some embodiments, the nonvolatile storage medium 660 may be configured as a first-in-first-out (FIFO) or last-in-first-out (LIFO) memory with respect to the stored measurement information.

In some embodiments, the measurement command execution process 500 may include a step 508 in which the sensor 100 conveys the measurement information. In one non-limiting embodiment, in step 508, the measurement controller 532 may output the measurement information to the data and control bus 654. The data and control bus 654 may transfer the measurement information to the command decoder/data encoder 652, which may encode the measurement information. The data serializer 656 may serialize the encoded measurement information. The encoder 658 may encode the serialized measurement information. The clamp/modulator 646 may modulate the current flowing through the inductive element 114 (e.g., coil 220) as a function of the encoded measurement information. In this way, the encoded measurement information may be conveyed wirelessly by the inductive element 114 as a modulated electromagnetic wave. In some embodiments, the encoded measurement information wirelessly conveyed by the sensor 100 may be received by the sensor transceiver 101, which may display the received measurement information (e.g., as a value representing the concentration of the analyte) so that a user (e.g., the patient, a doctor and/or others) can read the measurement information.

In some embodiments, the measurement command execution process 600 that may be performed in step 406 of the sensor control process 400 by the sensor 100 to execute a measurement command received by the sensor 100 may be completed, and, at this time, the sensor control process 400 may return to step 410.

Figure 6:
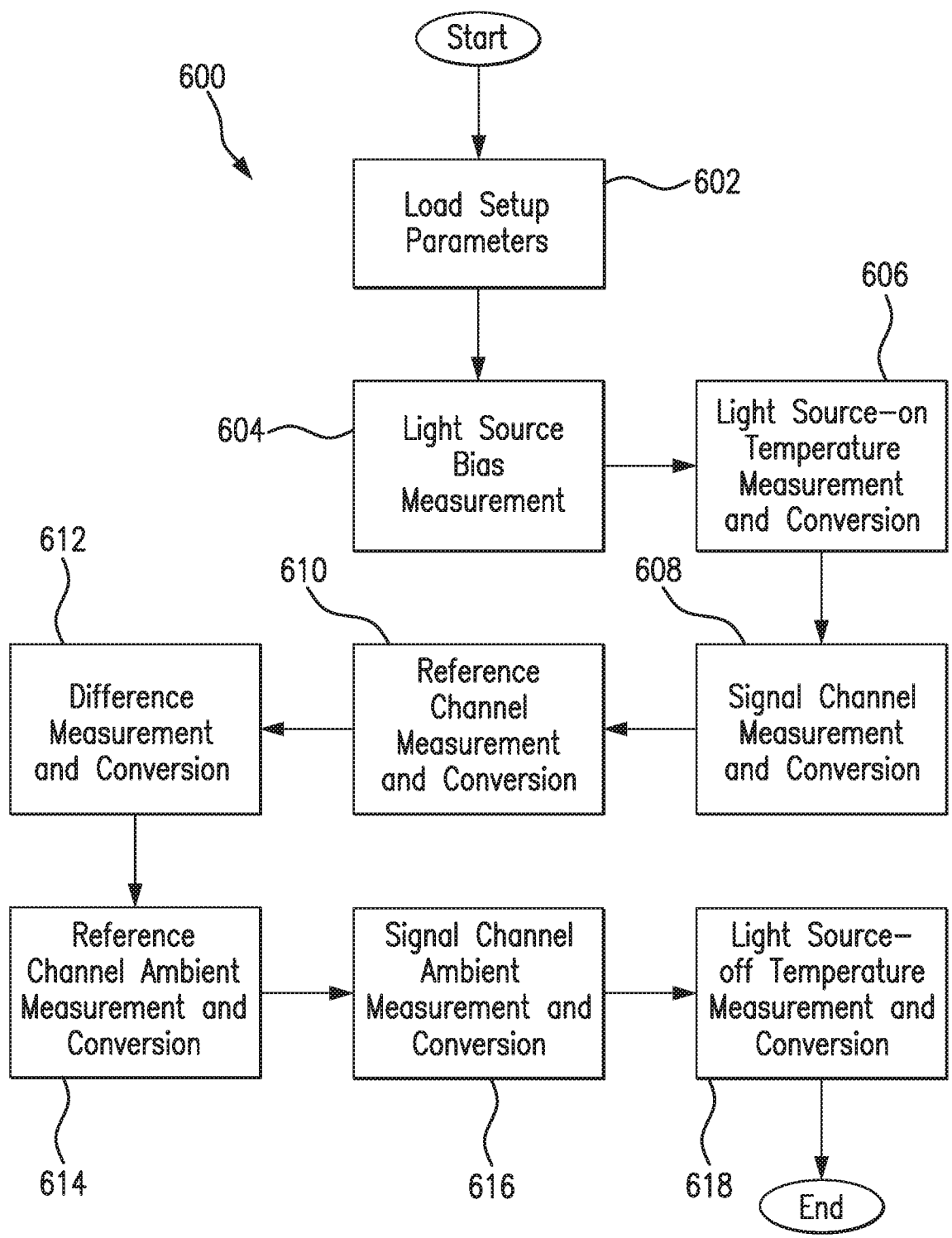
FIG. 6 illustrates a measurement and conversion process that may be performed in a step of the measurement command execution process, in accordance with an embodiment of the present invention.

FIG. 6 illustrates a measurement and conversion process 600, which is an example of the measurement and conversion process that may be performed in step 502 of the measurement command execution process 500, in accordance with an embodiment of the present invention.

At step 602, the sensor 100 may load setup parameters (i.e., calibration information) for performing one or more measurements in accordance with the received measurement command. For example, in one embodiment, the measurement controller 532 may load one or more setup parameters by setting up one or more components (e.g., light source 108, first photodetector 224, second photodetector 226, comparator 668 and/or temperature transducer 534) of the analog interface 534 with the setup parameters. In some embodiments, the nonvolatile storage medium 660 may store saved setup parameters. Further, as noted above, in some embodiments, the measurement commands may or may not include setup parameters. In a non-limiting embodiment, if the measurement command includes one or more setup parameters, the measurement controller 532 may setup one or more components of the analog interface 534 with the setup parameters with the one or more setup parameters included in the measurement command. However, if the measurement command does not include one or more setup parameters, the measurement controller 532 may obtain saved setup parameters stored in the nonvolatile storage medium 660 and setup one or more components of the analog interface 534 with the saved setup parameters obtained from the nonvolatile storage medium 660.

At step 604, the sensor 100 may perform a light source bias measurement and conversion. For example, in some embodiments, while the light source 108 is on (i.e., while the light source 108, under the control of the measurement controller 532, is emitting excitation light 329 and irradiating indicator molecules 104), the analog interface 534 may generate an analog light source bias measurement signal. In one embodiment, the ADC 664 may convert the analog light source bias measurement signal to a digital light source bias measurement signal. The measurement controller 532 may receive the digital light source bias measurement signal and generate (e.g., in step 504 of the measurement command execution process 500) the measurement information in accordance with the received digital light source bias measurement signal. In a non-limiting embodiment, the analog interface 534 may generate the analog light source bias measurement signal by sampling the voltage and the current in the output of the current source that feeds the light source 108.

At step 606, the sensor 100 may perform a light source-on temperature measurement and conversion. For example, in some embodiments, while the light source 108 is on (i.e., while the light source 108, under the control of the measurement controller 532, is emitting excitation light and irradiating indicator molecules 104), the analog interface 534 may generate a first analog temperature measurement signal indicative of a temperature of the sensor 100. In one embodiment, the temperature transducer 670 may generate the first analog temperature measurement signal while the light source 108 is on. The ADC 664 may convert the first analog temperature measurement signal to a first digital temperature measurement signal. The measurement controller 532 may receive the first digital temperature measurement signal and generate (e.g., in step 504 of the measurement command execution process 500) the measurement information in accordance with the received first digital temperature measurement signal.

At step 608, the sensor 100 may perform a first photodetector measurement and conversion. For example, in some embodiments, while the light source 108 is on (i.e., while the light source 108, under the control of the measurement controller 532, is emitting excitation light and irradiating indicator molecules 104), the first photodetector 224 may generate a first analog light measurement signal indicative of the amount of light received by the first photodetector 224 and output the first analog light measurement signal to the signal MUX 666. The signal MUX 666 may select the first analog light measurement signal and, the ADC 664 may convert the first analog light measurement signal to a first digital light measurement signal. The measurement controller 532 may receive the first digital light measurement signal and generate (e.g., in step 504 of the measurement command execution process 500) the measurement information in accordance with the received first digital light measurement signal.

In a non-limiting embodiment, first photodetector 224 may be a part of a signal channel, the light 331 received by the first photodetector 224 may be emitted by indicator molecules 104 distributed in the polymer graft 106, and the first analog light measurement signal may be an indicator measurement.

At step 610, the sensor 100 may perform a second photodetector measurement and conversion. For example, in some embodiments, while the light source 108 is on (i.e., while the light source 108, under the control of the measurement controller 532 is emitting excitation light and irradiating indicator molecules 104), the second photodetector 226 may generate a second analog light measurement signal indicative of the amount of light received by the second photodetector 226 and output the second analog light measurement signal to the signal MUX 666. The signal MUX 666 may select the second analog light measurement signal and, the ADC 664 may convert the second analog light measurement signal to a second digital light measurement signal. The measurement controller 532 may receive the second digital light measurement signal and generate (e.g., in step 504 of the measurement command execution process 500) the measurement information in accordance with the received second digital light measurement signal.

In a non-limiting embodiment, second photodetector 226 may be a part of a reference channel, the light 333 received by the second photodetector 226 may be reflected by the polymer graft 106, and the second analog light measurement signal may be a reference measurement. However, this is not required, and, for example, in one alternative embodiment, the light 333 received by the second photodetector 226 may be emitted by reference indicator molecules (e.g., in polymer graft 106) that are unaffected or generally unaffected by the presence and/or concentration of the analyte.

At step 612, the sensor 100 may perform a difference measurement and conversion. For example, in some embodiments, while the light source 108 is on (i.e., while the light source 108, under the control of the measurement controller 532, is emitting excitation light and irradiating indicator molecules 104), (i) the first photodetector 224 may generate a first analog light measurement signal indicative of the amount of light received by the first photodetector 224, and (ii) the second photodetector 226 may generate a second analog light measurement signal indicative of the amount of light received by the second photodetector 226. The comparator 668 may receive the first and second analog light measurement signals and generate an analog light difference measurement signal indicative of a difference between the first and second analog light measurement signals. The comparator 668 may output the analog light difference measurement signal to the signal MUX 666. The signal MUX 666 may select the analog light difference measurement signal and, the ADC 664 may convert the analog light difference measurement signal to a digital light difference measurement signal. The measurement controller 532 may receive the digital light difference measurement signal and generate (e.g., in step 504 of the measurement command execution process 500) the measurement information in accordance with the received digital light difference measurement signal.

In a non-limiting embodiment, first photodetector 224 may be a part of a signal channel, second photodetector 226 may be a part of a reference channel, and the analog light difference measurement signal may be indicative of the difference in (a) light emitted by indicator molecules 104 distributed in polymer graft 106 and affected by the concentration of an analyte in the medium in which sensor 100 is implanted, and (b) excitation light reflected by the polymer graft 106 and unaffected or generally unaffected by the concentration of the analyte in the medium in which sensor 100 is implanted. However, this is not required, and, for example, in one alternative embodiment, the analog light difference measurement signal may be indicative of the difference in (a) light emitted by indicator molecules 104 distributed in polymer graft 106 and affected by the concentration of an analyte in the medium in which sensor 100 is implanted, and (b) light emitted by reference indicator molecules (e.g., in polymer graft 106) that are unaffected or generally unaffected by the presence and/or concentration of the analyte.

At step 614, the sensor 100 may perform a second photodetector ambient measurement and conversion. For example, in some embodiments, while the light source 108 is off (i.e., while the light source 108, under the control of the measurement controller 532 is not emitting light), the second photodetector 226 may generate a second analog ambient light measurement signal indicative of the amount of light received by the second photodetector 226 and output the second analog ambient light measurement signal to the signal MUX 666. The signal MUX 666 may select the second analog ambient light measurement signal and, the ADC 664 may convert the second analog ambient light measurement signal to a second digital ambient light measurement signal. The measurement controller 532 may receive the second digital ambient light measurement signal and generate (e.g., in step 504 of the measurement command execution process 500) the measurement information in accordance with the received second digital ambient light measurement signal.

At step 616, the sensor 100 may perform a first photodetector ambient measurement and conversion. For example, in some embodiments, while the light source 108 is off (i.e., while the light source 108, under the control of the measurement controller 532, is not emitting light), the first photodetector 224 may generate a first analog ambient light measurement signal indicative of the amount of light received by the first photodetector 224 and output the first analog ambient light measurement signal to the signal MUX 666. The signal MUX 666 may select the first analog ambient light measurement signal and, the ADC 664 may convert the first analog ambient light measurement signal to a first digital ambient light measurement signal. The measurement controller 532 may receive the first digital ambient light measurement signal and generate (e.g., in step 504 of the measurement command execution process 500) the measurement information in accordance with the received first digital ambient light measurement signal.

At step 618, the sensor 100 may perform a light source-off temperature measurement and conversion. For example, in some embodiments, while the light source 108 is off (i.e., while the light source 108, under the control of the measurement controller 532, is not emitting light), the analog interface 534 may generate a second analog temperature measurement signal indicative of a temperature of the sensor 100. In one embodiment, the temperature transducer 670 may generate the second analog temperature measurement signal while the light source 108 is off. The ADC 664 may convert the second analog temperature measurement signal to a second digital temperature measurement signal. The measurement controller 532 may receive the second digital temperature measurement signal and generate (e.g., in step 504 of the measurement command execution process 500) the measurement information in accordance with the received second digital temperature measurement signal.

Accordingly, in an embodiment in which sequence steps 604-618 of measurement and conversion process 600 are performed, the measurement controller 532 may generate measurement information in accordance with (i) the first digital temperature measurement signal, (ii) the first digital light measurement signal, (iii) the second digital light measurement signal, (iv) the digital light difference measurement signal, (v) the second digital temperature measurement signal, (vi) the first digital ambient light measurement signal, and (vii) the second digital ambient light measurement signal. In a non-limiting embodiment, the calculation of the concentration of the analyte (e.g., performed by the measurement controller 532 of sensor 100 and/or sensor transceiver 101) may include subtracting the digital ambient light signals from the corresponding digital light measurement signals. The calculation of the concentration of the analyte may also include error detection. In some embodiments, the measurement controller 532 may incorporate methods for attenuating the effects of ambient light, such as, for example, those described in U.S. Pat. No. 7,227,156, which is incorporated herein by reference in its entirety.

In some embodiments, the measurement controller 532 may generate measurement information that merely comprises the digital measurement signals received from the analog interface 534. In some embodiments, the sensor 100 may convey the digital measurement signals to an external transceiver 101, and the external transceiver 101 may use the digital measurement signals to determine (i.e., calculate and/or estimate) the concentration of an analyte in the medium in which the sensor 100 is implanted. In some non-limiting embodiments, the analyte may be glucose, and the transceiver 101 may calculate glucose concentration in the manner described in U.S. Patent Application Publication No. 2014/0018644, which is incorporated by reference herein in its entirety. However, in some alternative embodiments, the measurement controller 532 may process the digital signals received from the analog interface 534 and determine (i.e., calculate and/or estimate) the concentration of an analyte in the medium in which the sensor 100 is implanted, and the measurement information may, additionally or alternatively, include the determined concentration. In some embodiments, the analyte may be glucose, and the measurement controller 532 may calculate glucose concentration in the manner described in U.S. Patent Application Publication No. 2013/0331667, which is incorporated by reference herein in its entirety.

In some embodiments, light source 108 may be turned on before execution of step 604 and not turned off until after execution of step 612. However, this is not required. For example, in other embodiments, the light source 108 may be turned on during measurement portions of steps 604-612 and turned off during the conversion portions of steps 604-612.

Furthermore, although FIG. 6 illustrates one possible sequence of the measurement and conversion process 600, it is not necessary that steps 604-618 of the measurement and conversion process 600 be performed in any particular sequence. For example, in one alternative embodiment, light measurement and conversion steps 604-612 may be performed in a different order (e.g., 606, 610, 612, 608, 604), and/or ambient light measurement and conversion steps 614-618 may be performed in a different order (e.g., 616, 618, 614). In some embodiments, the light source on temperature measurement may be used to provide an error flag in each individual measurement (e.g., by using a comparator to comparing the light source on temperature measurement to threshold value). In another alternative embodiment, ambient light measurement and conversion steps 614-618 may be performed before light measurement and conversion steps 604-612. In still another alternative embodiment, steps 604-618 of the measurement and conversion process 600 may be performed in a sequence in which all of the steps of one of light measurement and conversion steps 604-612 and ambient light measurement and conversion steps 614-618 are completed before one or more steps of the other are executed (e.g., in one embodiment, steps 604-618 may be performed in the sequence 604, 606, 608, 616, 614, 610, 612, 618). Also, in yet another alternative embodiment, the sensor 100 may perform only a portion (i.e., less than all) of measurement and conversion sequence steps 604-618 and/or additional measurement and conversion sequence steps.

Figure 7A:
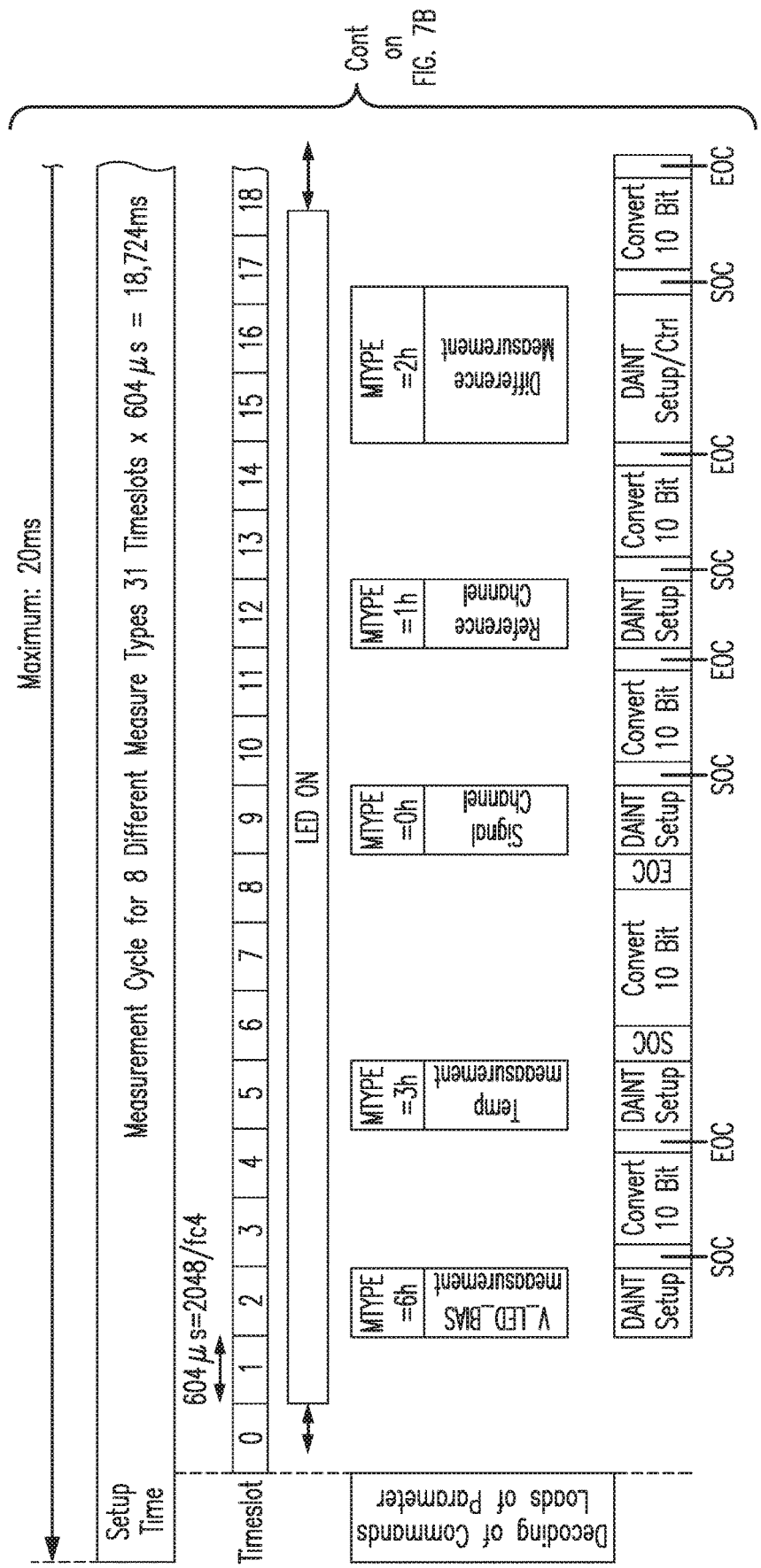
FIGS. 7A and 7B illustrate the timing of an exemplary embodiment of a measurement and conversion process in accordance with an embodiment of the present invention.
Figure 7B:
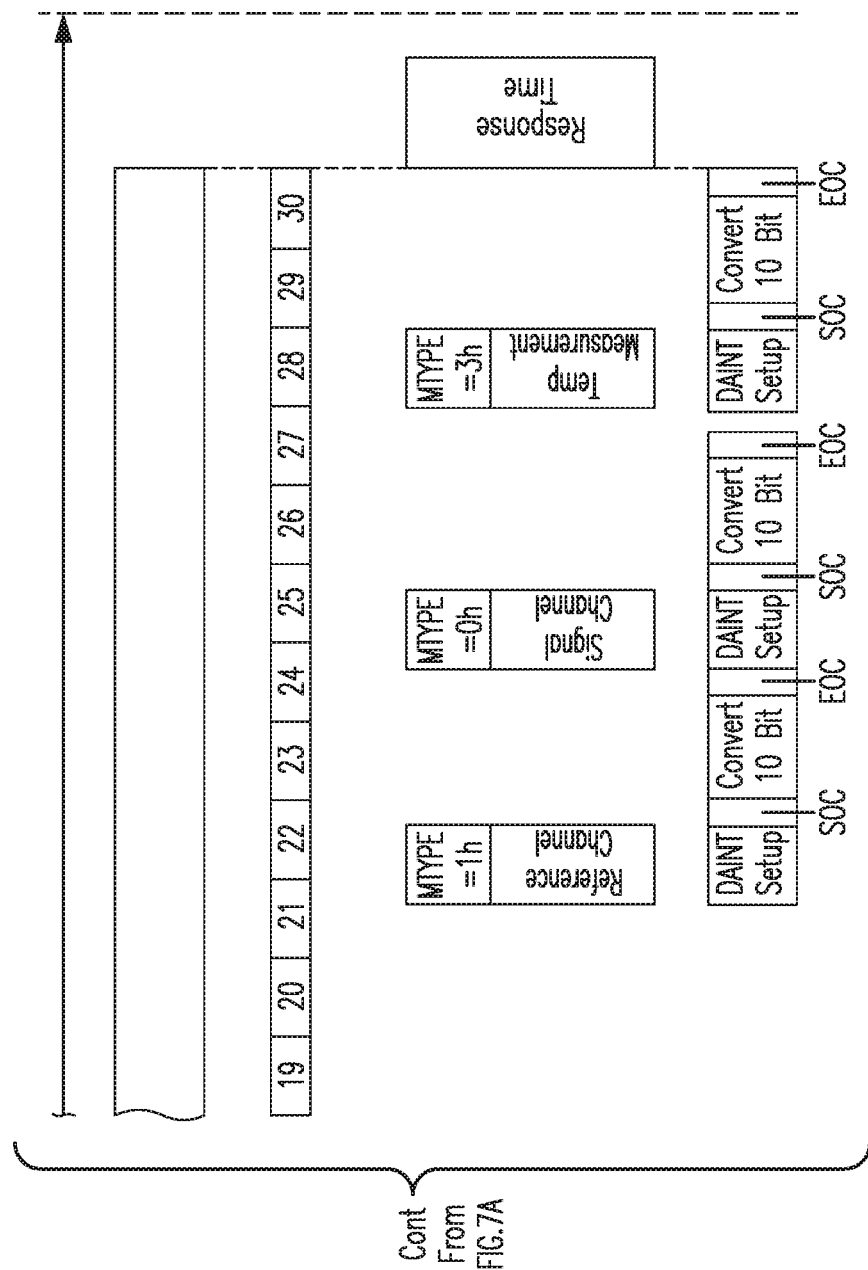

FIGS. 7A and 7B illustrates the timing of an exemplary embodiment of the measurement and conversion process 600 described with reference to FIG. 6.

In addition, when a new transceiver 101 is used with an implanted sensor 100, the new transceiver 101 may not have sensor calibration parameters and/or information regarding user preferences/settings. In some embodiments, calibration parameters and information regarding user preferences/settings may be stored in the sensor 100 (e.g., in the non-volatile storage medium 660), and the sensor 100 may convey the stored calibration parameters and/or information regarding user preferences/settings to the new transceiver 101 (e.g., after determining the transceiver ID from the new transceiver 101 is a new or different transceiver ID (see step 412 of FIG. 4). In some embodiments, the calibration parameters and information regarding user preferences/settings may additionally or alternatively be stored in an external memory stick (e.g., USB or Secure Digital (SD) card) or smartphone that is utilized with an external transceiver 101 before switching to the new external transceiver 101. In some embodiments, the calibration parameters and information regarding user preferences/settings may additionally or alternatively be stored on a web portal. The new external transceiver 101 may receive/download the calibration parameters and/or information regarding user preferences/settings from the sensor, external memory stick, smartphone, or web portal using wired or wireless connection. Accordingly, multiple transceivers 101 may be used with an implanted sensor 100 throughout the lifetime of the sensor 100 without having to reinitiate a calibration process and/or adjust the transceiver to the user preferred setting each time the a new transceiver 101 is used with the sensor 100.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, the circuitry of the sensor 100 may be implemented in hardware, software, or a combination of hardware and software. The software may be implemented as computer executable instructions that, when executed by a processor, cause the processor to perform one or more functions. Also, although the present invention has been described with reference to specific embodiments having a sensor and transceivers, the present invention is not limited to systems having a sensor and transceivers and is additionally applicable to any communication system having one node that communicates with one or more other nodes each having a unique identification code.

For another example, although in some embodiments, as illustrated in FIGS. 1 and 2, the sensor 100 may be an optical sensor, this is not required, and, in one or more alternative embodiments, sensor 100 may be a different type of analyte sensor, such as, for example, a diffusion sensor or a pressure sensor. Also, although in some embodiments, as illustrated in FIGS. 1 and 2, the analyte sensor 100 may be a fully implantable sensor, this is not required, and, in some alternative embodiments, the sensor 100 may be a transcutaneous sensor having a wired connection to the transceiver 101. For example, in some alternative embodiments, the sensor 100 may be located in or on a transcutaneous needle (e.g., at the tip thereof). In these embodiments, instead of wirelessly communicating using inductive elements 103 and 114, the sensor 100 and transceiver 101 may communicate using one or more wires connected between the transceiver 101 and the transceiver transcutaneous needle that includes the sensor 100. For another example, in some alternative embodiments, the sensor 100 may be located in a catheter (e.g., for intravenous blood glucose monitoring) and may communicate (wirelessly or using wires) with the transceiver 101.

What is claimed is:

1. A method of using a first node in a system having two or more nodes, the method comprising:
   receiving, using the first node, a unique identification code from a second node in the system, wherein the unique identification code identifies the second node;
   determining, using the first node, that the second node has not previously communicated with the first node based on the received unique identification code;
   if the second node is determined to have not previously communicated with the first node, storing, using the first node, the received unique identification code in a nonvolatile storage medium of the first node; and
   if the second node is determined to have not previously communicated with the first node, conveying, using the first node, information stored in the nonvolatile storage medium of the first node to the second node.

2. The method of claim 1, wherein the first node is a sensor in a living animal, and the second node is a transceiver external to the living animal.

3. The method of claim 1, wherein the first node is a smartphone, and the second node is a transceiver.

4. The method of claim 3, wherein the transceiver is external to a living animal and in communication with a sensor in the living animal and the smartphone.

5. System comprising:
   a first node configured to convey a first unique identification (ID);
   a second node configured to convey a second unique ID;
   a third node including circuitry, wherein the circuitry includes a non-volatile storage medium and is configured to:
     receive the first unique ID conveyed from the first node;
     store the received first unique ID in the nonvolatile storage medium;
     receive the second unique ID conveyed from the second node;
     determine that the received second unique ID is a new unique ID by comparing the received second unique ID to the stored first unique ID;
     store the received second unique ID in the nonvolatile storage medium; and
     convey information stored in the nonvolatile storage medium to the second node.

6. The system of claim 5, wherein the first unique ID identifies the first node, and the second unique ID identifies the second node.

7. The method of claim 1, wherein determining that the second node has not previously communicated with the first node based on the received unique identification code comprises determining that the received unique identification code does not match any unique identification code previously stored to the nonvolatile storage medium of the first node.

8. The method of claim 1, wherein the first node conveys the information to the second node only if the second node is determined to have not previously communicated with the first node.

9. A first node in a system having two or more nodes, the first node comprising:
   an inductive element;
   circuitry including a non-volatile storage medium, wherein the circuitry is configured to:
     use the inductive element to receive a unique identification code from a second node in the system, wherein the unique identification code identifies the second node;
     determine that the second node has not previously communicated with the first node based on the received unique identification code;
     if the second node is determined to have not previously communicated with the first node, store the received unique identification code in the nonvolatile storage medium; and
     if the second node is determined to have not previously communicated with the first node, convey, using the inductive element, information stored in the nonvolatile storage medium to the second node.

10. The first node of claim 9, wherein the circuitry is configured to determine that the second node has not previously communicated with the first node based on the received unique identification code by determining that the received unique identification code does not match any unique identification code previously stored to the nonvolatile storage medium.

11. The first node of claim 9, wherein the circuitry is configured to convey the information to the second node only if the second node is determined to be a new node that has not previously communicated with the first node.

12. A method of using a first node in a system having two or more nodes, the method comprising:

receiving, using the first node, a unique identification code from a second node in the system, wherein the unique identification code identifies the second node, the first node is a sensor in a living animal, and the second node is a transceiver external to the living animal;

determining, using the first node, that the second node has not previously communicated with the first node based on the received unique identification code, wherein determining that the second node has not previously communicated with the first node comprises determining that the received unique identification code does not match any unique identification code previously stored to a nonvolatile storage medium of the first node.

13. A method of using a first node in a system having two or more nodes, the method comprising:

receiving, using the first node, a unique identification code from a second node in the system, wherein the unique identification code identifies the second node, the first node is a smartphone, and the second node is a transceiver;

determining, using the first node, that the second node has not previously communicated with the first node based on the received unique identification code, wherein determining that the second node has not previously communicated with the first node comprises determining that the received unique identification code does not match any unique identification code previously stored to a nonvolatile storage medium of the first node.

* * * * *